(12) United States Patent
Connelly et al.

(10) Patent No.: US 7,808,642 B2
(45) Date of Patent: Oct. 5, 2010

(54) TURBIDIMETER WITH ULTRASONICALLY CLEANED COMPONENTS

(75) Inventors: Rowan Connelly, Fort Myers, FL (US); Paul Condon, Fort Myers, FL (US); Joel Leal, Fort Myers, FL (US)

(73) Assignee: HF Scientific, Inc., Fort Myers, FL (US)

( * ) Notice: Subject to any disclaimer, the term of this patent is extended or adjusted under 35 U.S.C. 154(b) by 0 days.

(21) Appl. No.: 12/215,776

(22) Filed: Jun. 30, 2008

(65) Prior Publication Data

US 2009/0009770 A1 Jan. 8, 2009

Related U.S. Application Data

(63) Continuation of application No. 10/972,849, filed on Oct. 25, 2004, now abandoned.

(60) Provisional application No. 60/513,857, filed on Oct. 24, 2003.

(51) Int. Cl.
*G01N 21/00* (2006.01)
(52) U.S. Cl. ................ 356/440; 356/442
(58) Field of Classification Search ......... 356/423–444, 356/244, 246, 338–339; 134/92, 154, 182–184, 134/57 R, 84, 88–89, 117–118, 137–138, 134/169 C, 1, 1.3, 2, 7, 32–34, 147–148, 134/199, 902; 29/25.35; 137/237; 310/328, 310/322, 334
See application file for complete search history.

(56) References Cited

U.S. PATENT DOCUMENTS

| 1,936,259 | A | 11/1933 | Parmer |
|---|---|---|---|
| 3,522,436 | A | 8/1970 | Posgate |
| 3,937,236 | A | 2/1976 | Runnells |
| 3,968,459 | A | 7/1976 | Jacobson |
| 5,446,544 | A | 8/1995 | Beers |
| 5,748,566 | A | 5/1998 | Goodson |
| 6,426,794 | B1 | 7/2002 | Trainoff |
| 6,436,051 | B1 | 8/2002 | Morris et al. |
| 6,463,938 | B2 | 10/2002 | Bran |
| 2004/0054286 | A1 | 3/2004 | Audain et al. |
| 2004/0112413 | A1 | 6/2004 | Brunner et al. |

FOREIGN PATENT DOCUMENTS

| DE | 19741836 A1 | 3/1999 |
|---|---|---|
| WO | WO-02066267 | 8/2002 |

OTHER PUBLICATIONS

HF Scientific, Inc., "Micro TOL 0-1000 NTU"; Owner's Manual, Catalog No. 24031 (Dec. 2004) Rev. 2.7.

*Primary Examiner*—Gregory J Toatley
*Assistant Examiner*—Tri T Ton
(74) *Attorney, Agent, or Firm*—Edwards Angell Palmer & Dodge LLP; George N. Chaclas (57) ABSTRACT

An ultrasonic optical cleaning system is provided for cleaning and deterring the buildup of organic and inorganic particulates from the surface of glassware used in water testing instrumentation. The ultrasonic optical cleaning system includes a transducer that is attached to the surface of the glassware. A connector cap carrying a plurality of spring contacts interconnecting the transducer with an ultrasonic transducer control circuit. The control circuit operates continuously to provide an electrical signal to the transducer that vibrates the transducer and the glassware so that the glassware is cleaned of contaminates.

20 Claims, 9 Drawing Sheets

TURBIDIMETER WITH ULTRASONICALLY CLEANED COMPONENTS

CROSS-REFERENCE TO RELATED APPLICATIONS

This application claims the benefit of U.S. Provisional Patent Application Ser. No. 60/513,857 filed Oct. 24, 2003 and U.S. Utility patent application Ser. No. 10/972,849 filed Oct. 25, 2004, each of which is incorporated by reference in its entirety.

FIELD OF THE INVENTION

This invention relates to a system that ultrasonically cleans and deters the buildup of particulate matter on glassware of the type used in optical water testing equipment. The apparatus is particularly suited for use in cleaning a tube or cuvette that supports a water sample in a turbidimeter.

BACKGROUND OF THE INVENTION

Turbidimeters are widely utilized to test public water supplies for the presence of particulate matter suspended in the water. Examples of these instruments include the turbidimeter disclosed in U.S. Pat. No. 5,446,544 (the '544 patent), as well as the updated version distributed by HF Scientific, Inc. under the brand name MICRO TOL™. These and other varieties of turbidimeters typically employ a glass cuvette or tube that holds the water to be tested. Light is directed through the test sample and turbidity is electronically calculated and displayed.

In more detail, the '544 patent discloses a turbidimeter 10 that operably connects to a water filtration system. The turbidimeter 10 includes a light source module 50 that produces a beam of light. The test sample is placed in the path of the light and a photodetector or analogous sensor 18 is positioned to sense light scattered by and/or passing through the test sample. Circuitry or an analyzer responds to the photodetector to produce a turbidity measurement.

The MICRO TOL™ instrument is a wall-mounted turbidimeter that allows measuring process water turbidity on-line using long life infrared lamps. The MICRO TOL™ instrument is plumbed into a water filtration system to display turbidity measurements. Periodically, the cuvette of the MICRO TOL™ instrument must be cleaned. The MICRO TOL™ instrument comes with an Owners Manual that discusses how to manually clean the cuvette in section 9.1.

Over time, inorganic particulates and organic contaminates such as algae tend to build up on the surface of the glassware holding the test sample. If the cuvette is not cleaned, the dirt can distort the measurements taken by the turbidimeter, which can produce erroneous readings. To avoid inaccurate test results, the user must frequently clean the glass and recalibrate the turbidimeter. This tends to be tedious, time consuming and inefficient. The user is likely to experience undesirable "down-time" as turbidity readings cannot be taken while the instrument is being serviced.

Currently, a cuvette or other glassware used for optical testing of water must be cleaned manually on a periodic basis. There are no known devices available that automatically and continuously clean the glassware so that improved measurement accuracy is achieved, but tedious maintenance and repeated service interruptions are avoided.

SUMMARY OF THE INVENTION

It is therefore an object of the present disclosure to provide an apparatus for automatically and continuously cleaning and deterring particulate build-up on the glassware that accommodates a test sample in a turbidimeter or other optical water-testing instrument. It is a further object of this disclosure to provide an ultrasonic optical cleaning system that significantly reduces the inefficiency, tedium and service interruptions associated with manual cleaning. It is a further object of this disclosure to provide an apparatus for ultrasonically cleaning turbidimeter glassware, which apparatus is not hardwired to the electronics of the turbidimeter so that the glassware can be conveniently indexed and/or removed for recalibration, as needed.

It is a further object of this disclosure to provide an apparatus that effectively and efficiently cleans the glassware used in a water-testing instrument so that improved, accurate water quality measurements are obtained.

It is a further object of this disclosure to provide an apparatus for ultrasonically cleaning a turbidimeter cuvette, which apparatus cleans and deters the buildup of both inorganic and organic contaminates so that the user does not have to manually clean the glassware and recalibration of the turbidimeter is significantly reduced.

This disclosure features an ultrasonic optical cleaning system for use with glassware of the type used in optical water testing equipment. The system includes an ultrasonic transducer that is secured to the glassware to be cleaned. The transducer includes a material that vibrates when a selected voltage is applied to the transducer. The transducer is electrically connected to an ultrasonic control circuit by means of a contact connector cap. The ultrasonic control circuit delivers an electrical signal through the connector cap to the transducer so that the transducer vibrates to clean particulate matter from the glassware and prevent the build-up of particulates on the surface of the glassware.

In a preferred embodiment, the ultrasonic transducer includes a disk composed of a piezoelectric ceramic that is juxtaposed against and bonded to a lower surface of an aluminum disk. Preferably, the aluminum disk has a larger diameter than the piezoelectric disk. The surface of the aluminum disk opposite to the surface that carries the piezoelectric disk may be bonded directly to the surface of the glassware, such as on the bottom of the glassware. As a result, the piezoelectric disk faces away from the surface of the glassware. The transducer is preferably secured to the glassware by an appropriate adhesive. The connector cap may include an upper portion that carries a plurality of contacts for electrically engaging the transducer. These may be spring contacts that are longitudinally retractable within the connector cap. An outer spring contact may be engagable with the aluminum disk and an inner spring contact may be interengagable with the piezoelectric disk. The upper surface of the cap may also include an annular wall that surrounds the contacts for receiving a lower end of the glassware. In this way, the glassware is held in place with the transducer engaging the contacts. Lower ends of the contacts may extend from a lower end of the connector cap and be wired or otherwise electrically connected to the ultrasonic control circuit.

The ultrasonic control circuit may comprise an ultrasonic printed circuit board that is operably mounted to the printed circuit board that controls operation of the water testing equipment. The ultrasonic control circuit may receive power from the principal operating circuit of the test equipment. The control circuit typically delivers a voltage through the connector cap to the transducer and sweeps through a series of frequencies over a predetermined time span. Typically, the frequencies include the resonant frequency for the transducer-cuvette assembly such that the transducer exhibits a maximum vibration and energy is transferred to the glassware at a sufficient level so that optimum cleaning is achieved. Because the glassware is maintained substantially free of organic and inorganic particulates, improved measurements of water quality are obtained. At the same time, maintenance requirements are reduced considerably.

It should be appreciated that the present invention can be implemented and utilized in numerous ways, including without limitation as a process, an apparatus, a system, a device, a method for applications now known and later developed or a computer readable medium. These and other unique features of the system disclosed herein will become more readily apparent from the following description and the accompanying drawings.

BRIEF DESCRIPTION OF THE DRAWINGS

Other objects, features and advantages will occur from the following description of a preferred embodiment and the accompanying drawings, in which.

DETAILED DESCRIPTION OF PREFERRED EMBODIMENTS

The present disclosure overcomes many of the prior art problems associated with optical measurement systems that require periodic cleaning. The advantages, and other features of the systems and methods disclosed herein, will become more readily apparent to those having ordinary skill in the art from the following detailed description of certain preferred embodiments taken in conjunction with the drawings which set forth representative embodiments of the present invention and wherein like reference numerals identify similar structural elements. Additionally, for clarity items have not been included in the Figures or have been represented somewhat schematically as would be appreciated by those of ordinary skill in the pertinent art. Unless otherwise specified, the illustrated embodiments can be understood as providing exemplary features of varying detail of certain embodiments, and therefore, unless otherwise specified, features, components, modules, elements, and/or aspects of the illustrations can be otherwise combined, interconnected, sequenced, separated, interchanged, positioned, and/or rearranged without materially departing from the disclosed systems or methods. Additionally, the shapes and sizes of components are also exemplary and unless otherwise specified, can be altered without materially affecting or limiting the disclosed technology.

Figure 1A:
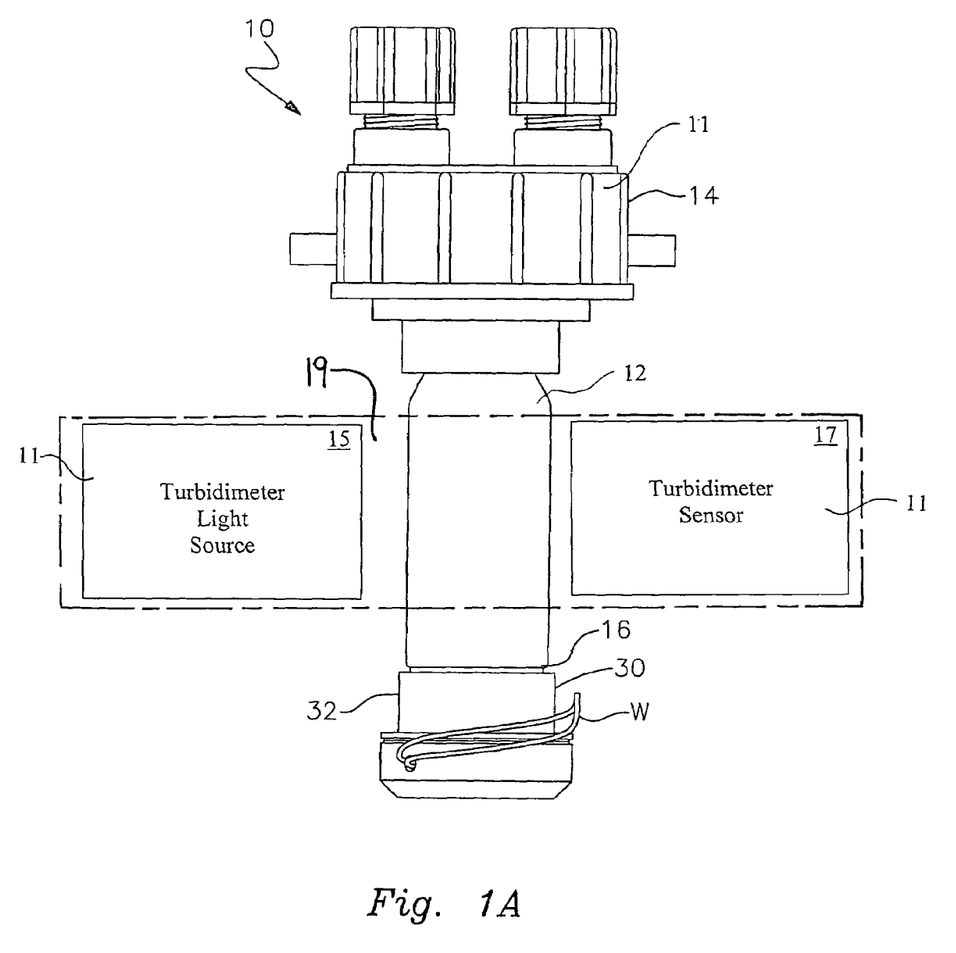
FIG. 1A is side elevational view of the ultrasonic optical cleaning system of this invention as used with a turbidimeter.
Figure 1B:
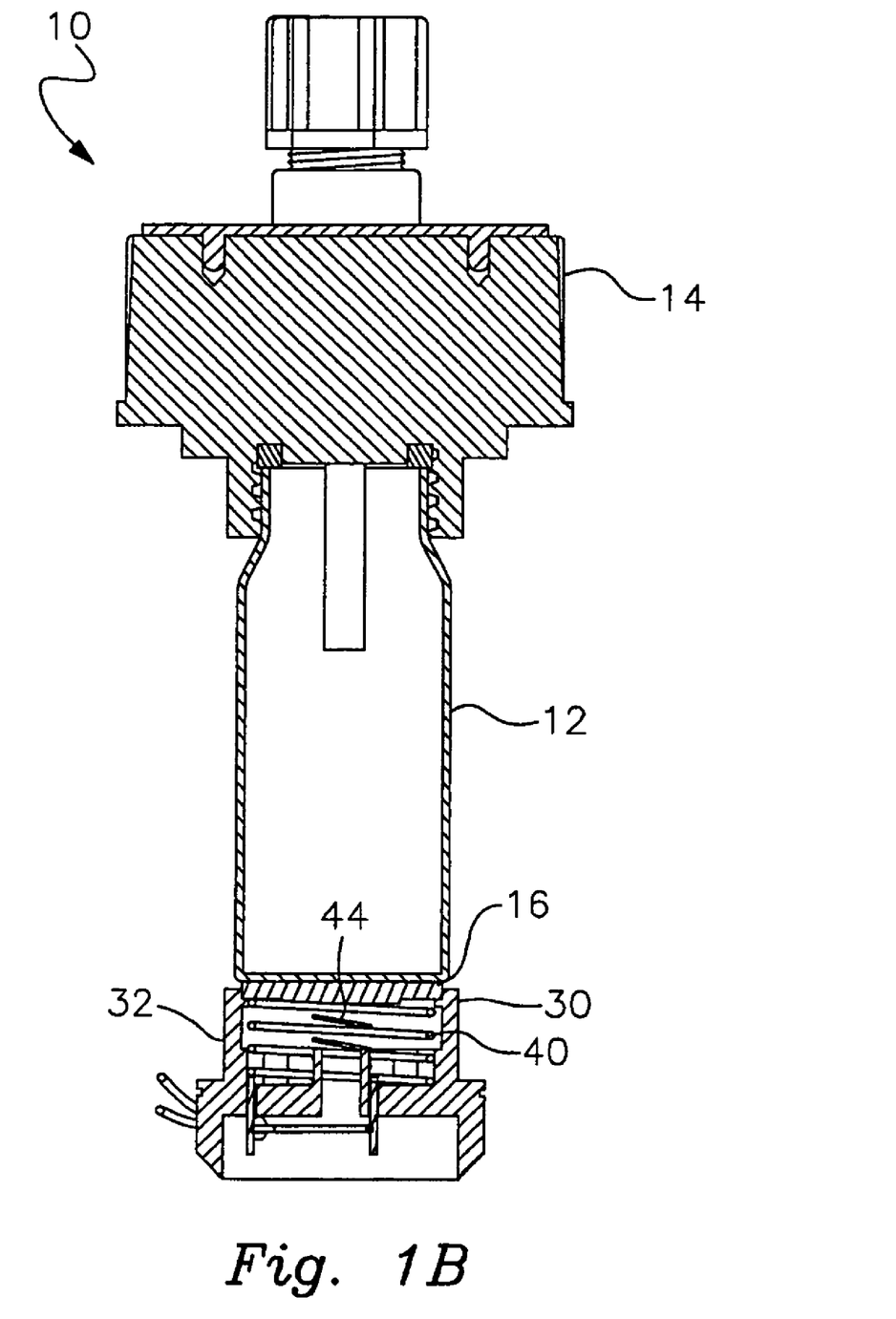
FIG. 1B is a cross sectional view of the cleaning system.

There is shown in FIGS. 1A and 1B an ultrasonic optical cleaning system 10 used for cleaning the glassware of a turbidimeter. In the version disclosed herein, the glassware comprises a conventional cuvette 12 of the type commonly employed in water quality testing equipment. This type of glassware may be used in a wide variety of optical instrumentation presently used in the water testing industry. Cuvettes of this type are used especially widely in turbidimeters such as the product disclosed in U.S. Pat. No. 5,446,544 and the previously referenced MICRO TOL™ turbidimeter. It should be understood, however, that cleaning system 10 is not limited to use with such products. The cleaning system may be used effectively in a wide range of optical test instruments and is suitable for cleaning all types of liquid-accommodating glassware. The particular type of instrumentation that uses the cleaning system does not constitute a limitation of this invention. It should also be noted that a wide variety of sizes and shapes of glassware may be utilized. These may include all types of glass cuvettes, tubes and other varieties of transparent containers.

In the embodiment depicted in FIGS. 1A and 1B, cuvette 12 is carried by a flow head 14. The turbidimeter 11 includes a measurement system 19 to measure the turbidity of a test sample in the cuvette 12. The measurement system 19 includes a light source 15 for directing light through the cuvette 12 and a sensor 17 for determining the turbidity of the test sample in the cuvette 12 by measuring the light passing there through from the light source 15 as is known to those of ordinary skill in the art. The cuvette 12 is supported so that these optical measurements may be taken and turbidity determined by the turbidimeter 11 without manual intervention. Over time, organic and inorganic particles tend to collect on the surface of the cuvette 12. These contaminates distort the optical measurements taken by the turbidimeter 11; as a result, the cuvette 12 normally has to be cleaned manually on a frequent and periodic basis. The cleaning system 10 is specifically designed to reduce the need for such periodic cleanings and resultant "down-time" and to enable the turbidimeter 11 to produce continuously accurate readings over a prolonged period of operation.

Figure 2:
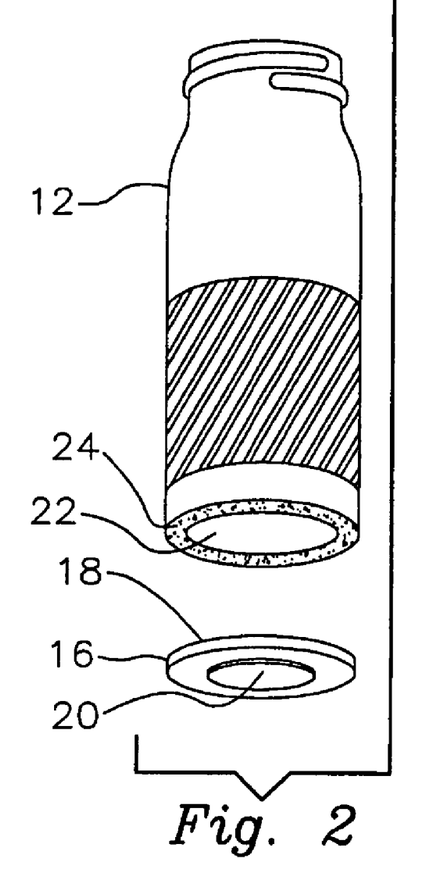
FIG. 2 is a perspective view of glassware comprising a cuvette and the ultrasonic transducer in position to be applied to the cuvette.
Figure 3:
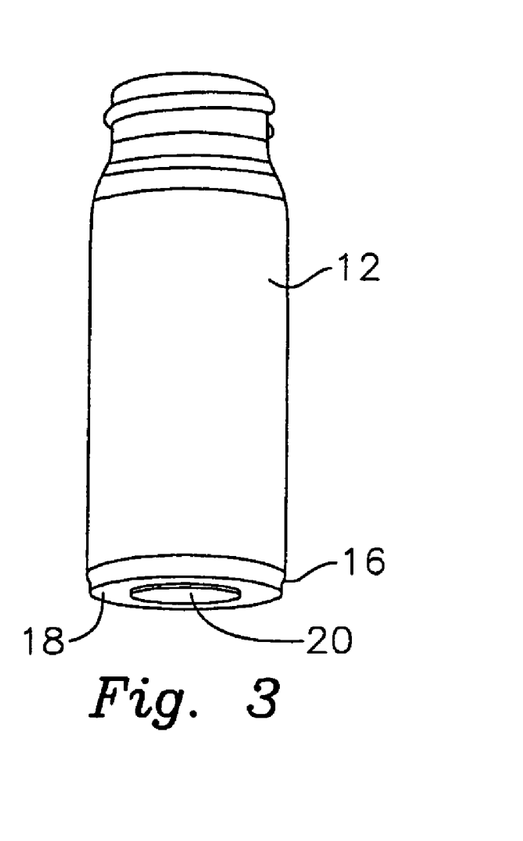
FIG. 3 is a view similar to FIG. 2 with the ultrasonic transducer bonded to a lower surface of glassware.

The cleaning system specifically includes an ultrasonic transducer 16, which is shown also in FIGS. 2 and 3. Transducer 16 includes a relatively large diameter aluminum disk 18 and a relatively small diameter piezoelectric ceramic (i.e. piezoceramic) disk 20 that is bonded to disk 18. More particularly, disk 20 is fastened to a lower surface of disk 18 by means of a suitable adhesive. This may include LOCTITE™ E-20HP epoxy or a similar product. Preliminarily, the lower surface 22 of cuvette 12 is roughened by using a coarse sandpaper or similar product. At least an outer ring 24 of lower surface 22 should exhibit deep scratches that facilitate bonding. The bottom of the cuvette is then cleaned with alcohol. The upper surface of the transducer (i.e. the upper surface of aluminum disk 18) is similarly cleaned. The adhesive is then applied between ring 24 of lower cuvette surface 22 and the upper surface of aluminum disk 18. Adhesive should not be applied to the lower surface of cuvette 12 within the area bounded by ring 24. The upper surface of the transducer is engaged against the lower surface of the cuvette and the adhesive is allowed to cure. As a result, the transducer is bonded to the lower surface of cuvette 12 in the manner shown in FIG. 3.

Figure 4:
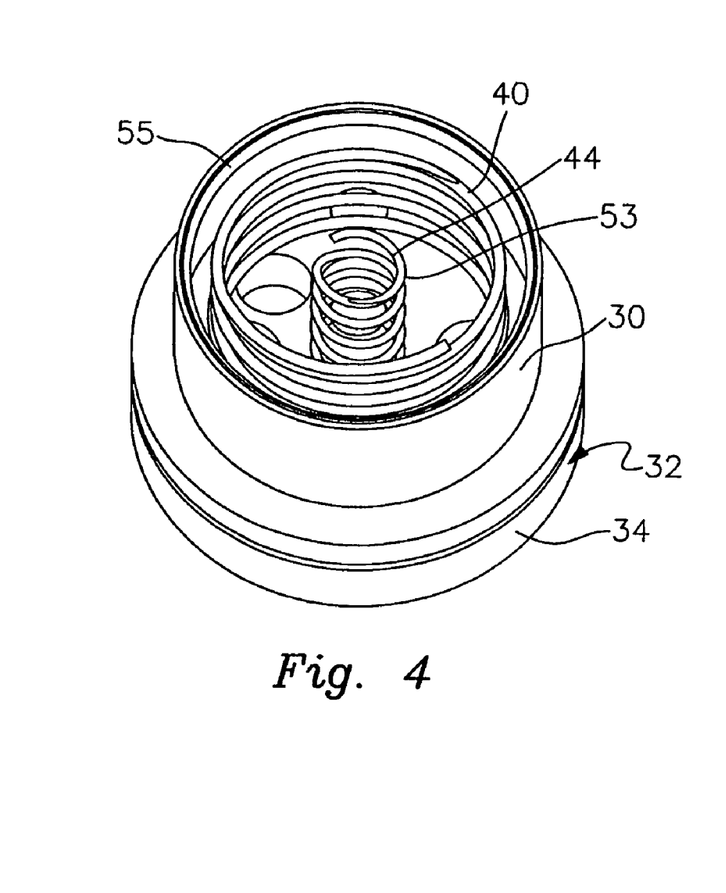
FIG. 4 is a perspective top view of the connector cap.
Figure 4A:
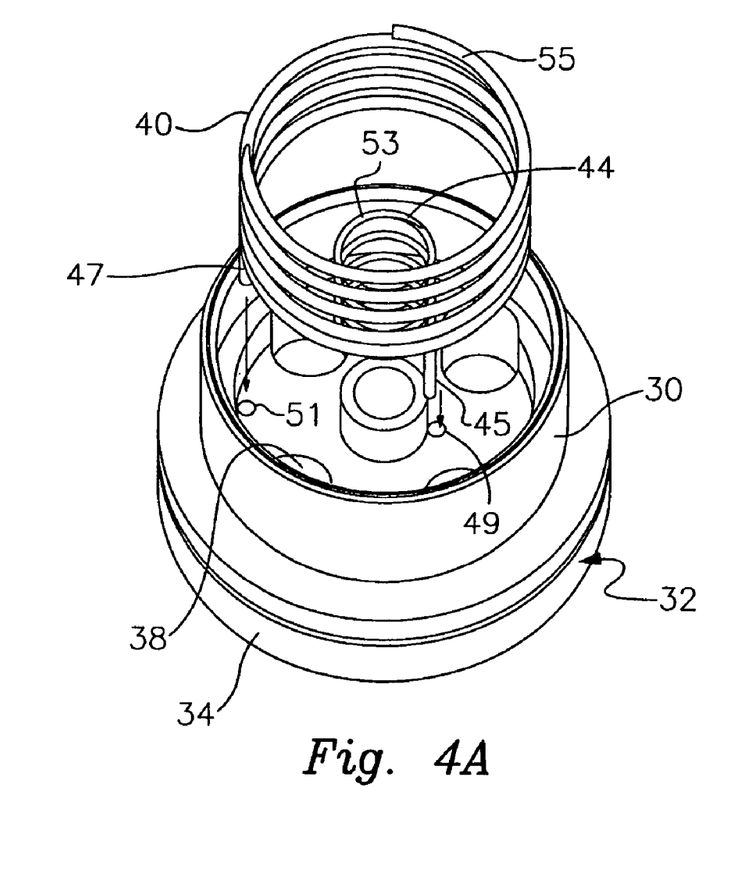
FIG. 4A is an exploded view of the connector cap.
Figure 5:
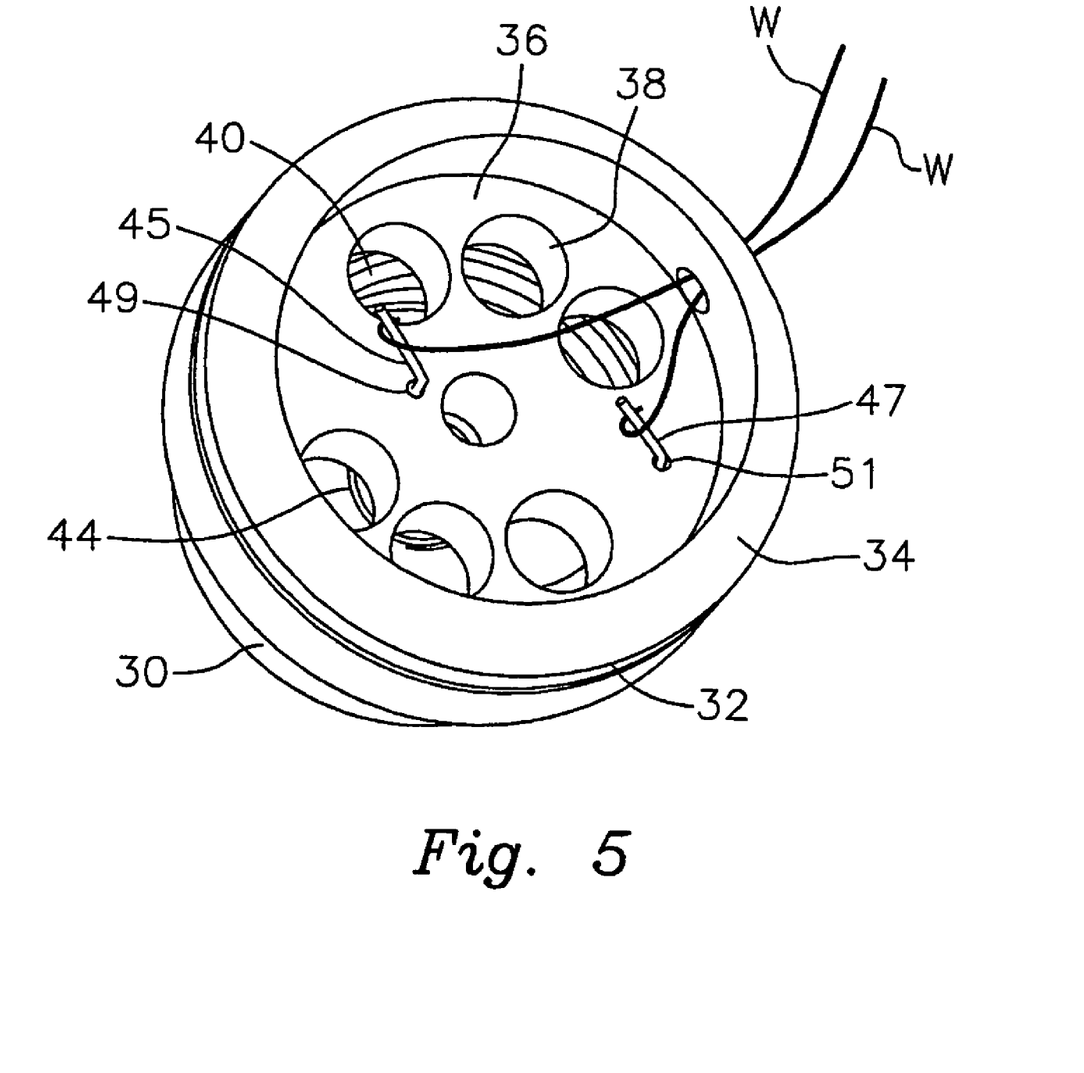
FIG. 5 is a bottom perspective view of the connector cap.

As shown in FIGS. 1A and 1B, the lower end of cuvette 12 and the ultrasonic transducer supported by the cuvette are received within a ring or annular lip 30 of a connector cap assembly 32. The connector cap assembly is shown alone in FIGS. 4, 4A and 5. In particular, the connector cap includes a generally circular base 34 having a recessed lower surface 36, FIG. 5. Ring 30 extends upwardly from an upper surface of base 34. A plurality of holes 38 are formed through the base such that the upper surface of the base communicates with the recessed lower surface of the base. Connector cap 32 is composed of a suitable plastic. Holes 38 reduce the amount of plastic required and also provide an emergency drain in the event of cuvette breakage. Connector cap 32 includes an outer coil spring contact 40 and an inner coil spring contact 44. These comprise respective coil springs which are mounted in base 34 of cap 32 such that they are longitudinally retractable relative to the base. The end posts 45 and 47 of spring contacts 40 and 44 respectively are received through respective holes 49, 51 in base 34 and bent as shown in FIG. 5 to hold contacts 40 and 44 in place. Each of the springs 40 and 44 is disposed within the area surrounded by ring 30. As best shown in FIGS. 4 and 4A, the upper end 53, 55 of each spring is ground flat for engaging transducer 16. As shown in FIG. 5, the lower ends of the springs protrude from the recessed region 36 of cap 32 and are connected through associated wiring W to a transducer control circuit, as is described more fully below. Other types of contacts, and preferably spring contacts, may be utilized within the scope of this invention.

Figure 6:
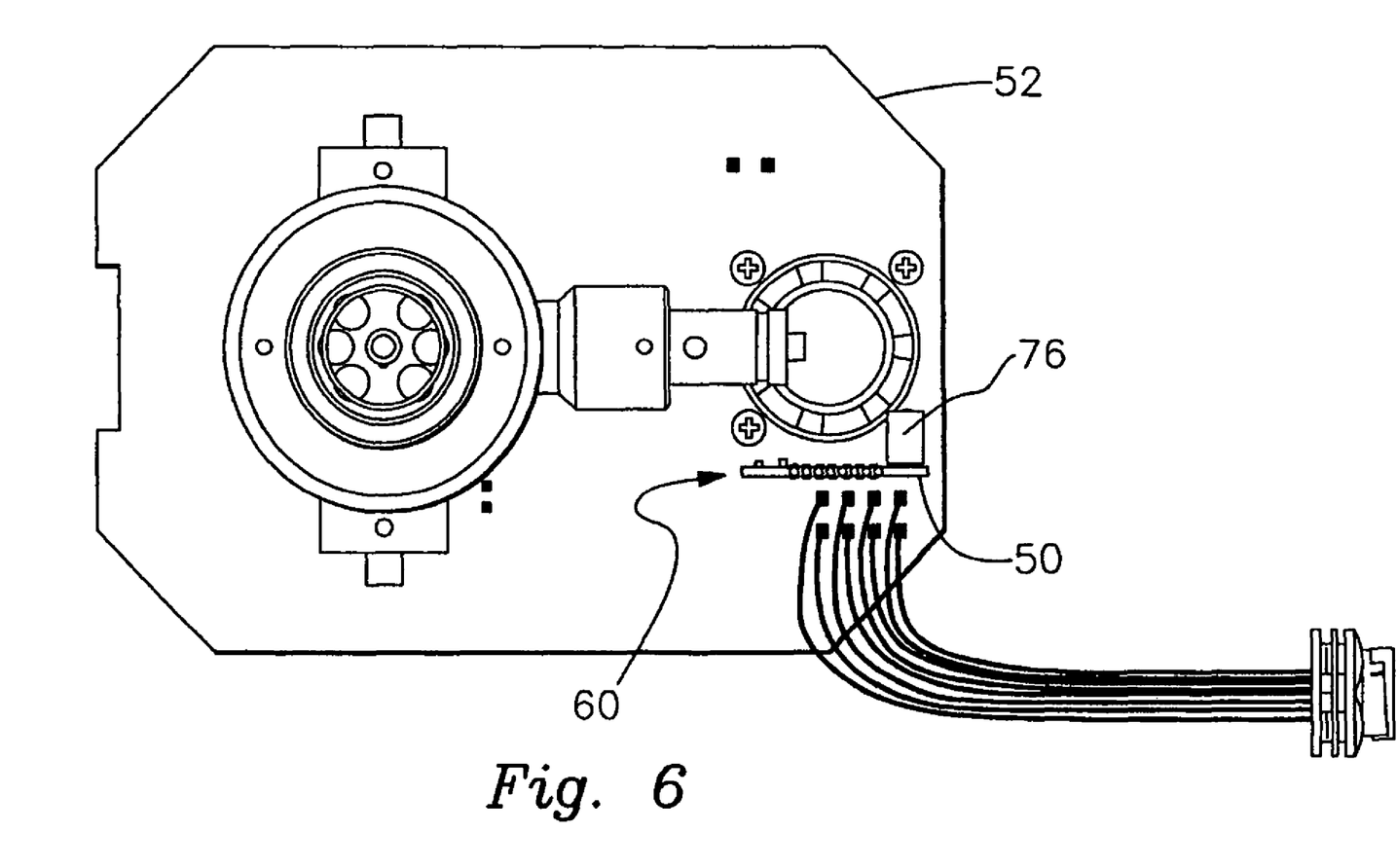
FIG. 6 is a plan view of the upper, component side of the main printed circuit board employed in a turbidimeter featuring the cleaning system of this invention; the ultrasonic printed circuit board is depicted as being mounted to the main board.
Figure 7:
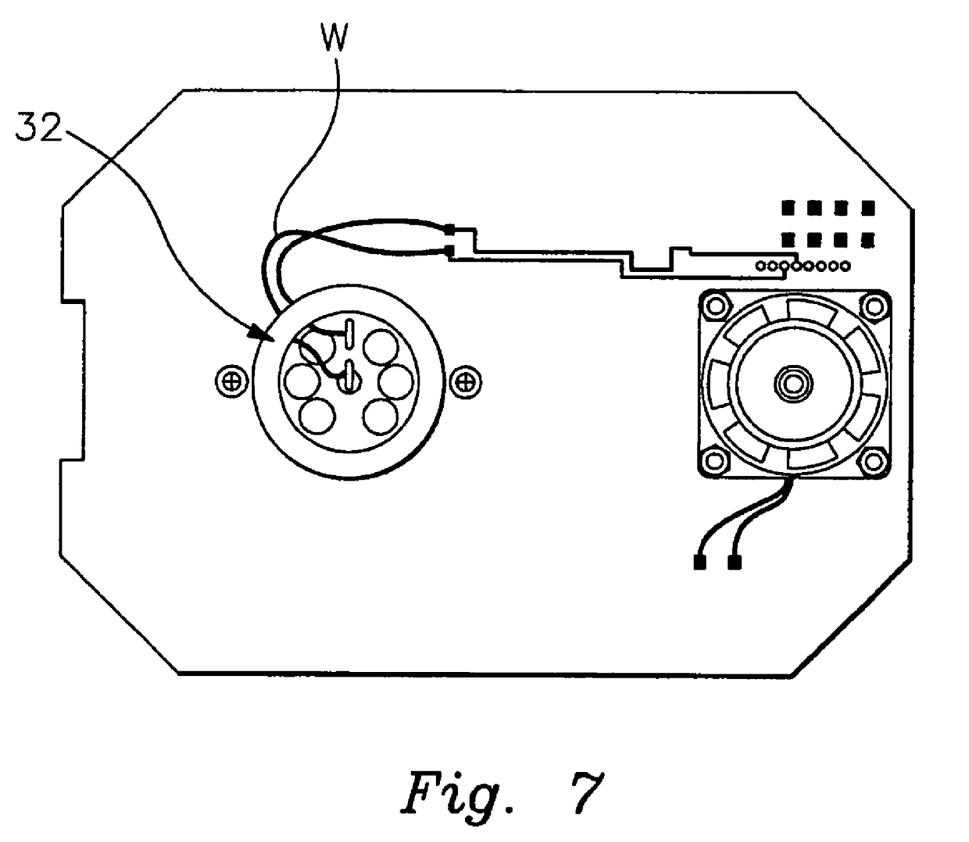
FIG. 7 is a plan view of the bottom, solder side of the main circuit board with the connector cap of the cleaning system attached thereto.

As shown in FIG. 6, an ultrasonic printed circuit board 50 is secured to the component side of the main printed circuit board 52 used to operate the turbidimeter. Board 50 supports an ultrasonic transducer control circuit 60, shown in detail in FIG. 8. More particularly, the components of circuit 60 are mounted on ultrasonic printed circuit board 50 in a conventional manner. Circuit 60 is electrically interconnected between the microcontroller and power supply of the main circuit board 52 and the wiring W that joins circuit 60 to connector cap 32. (See FIGS. 7 and 8).

Figure 8A:
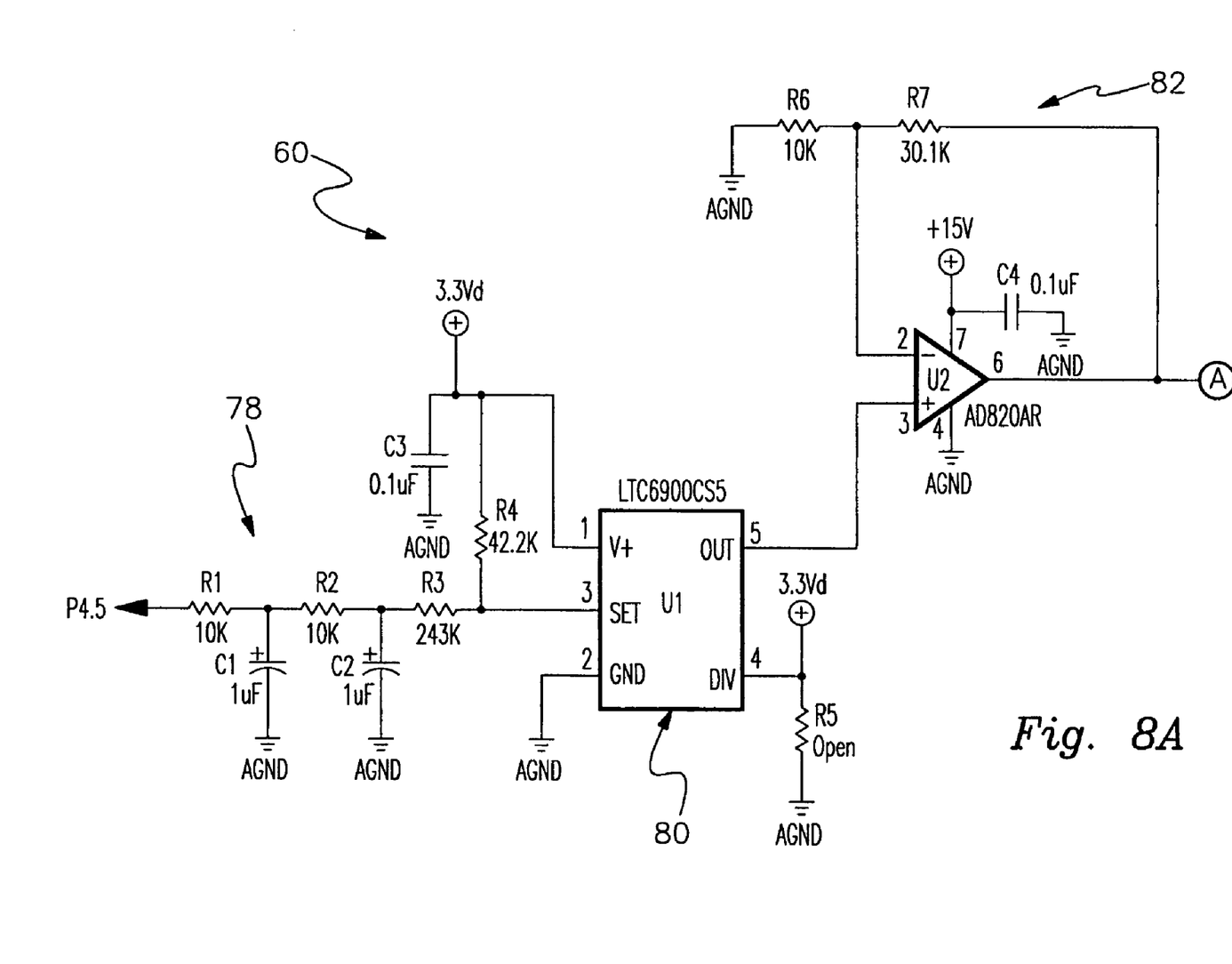
FIG. 8 is a schematic view of a preferred version of the ultrasonic control circuit.
Figure 8B:
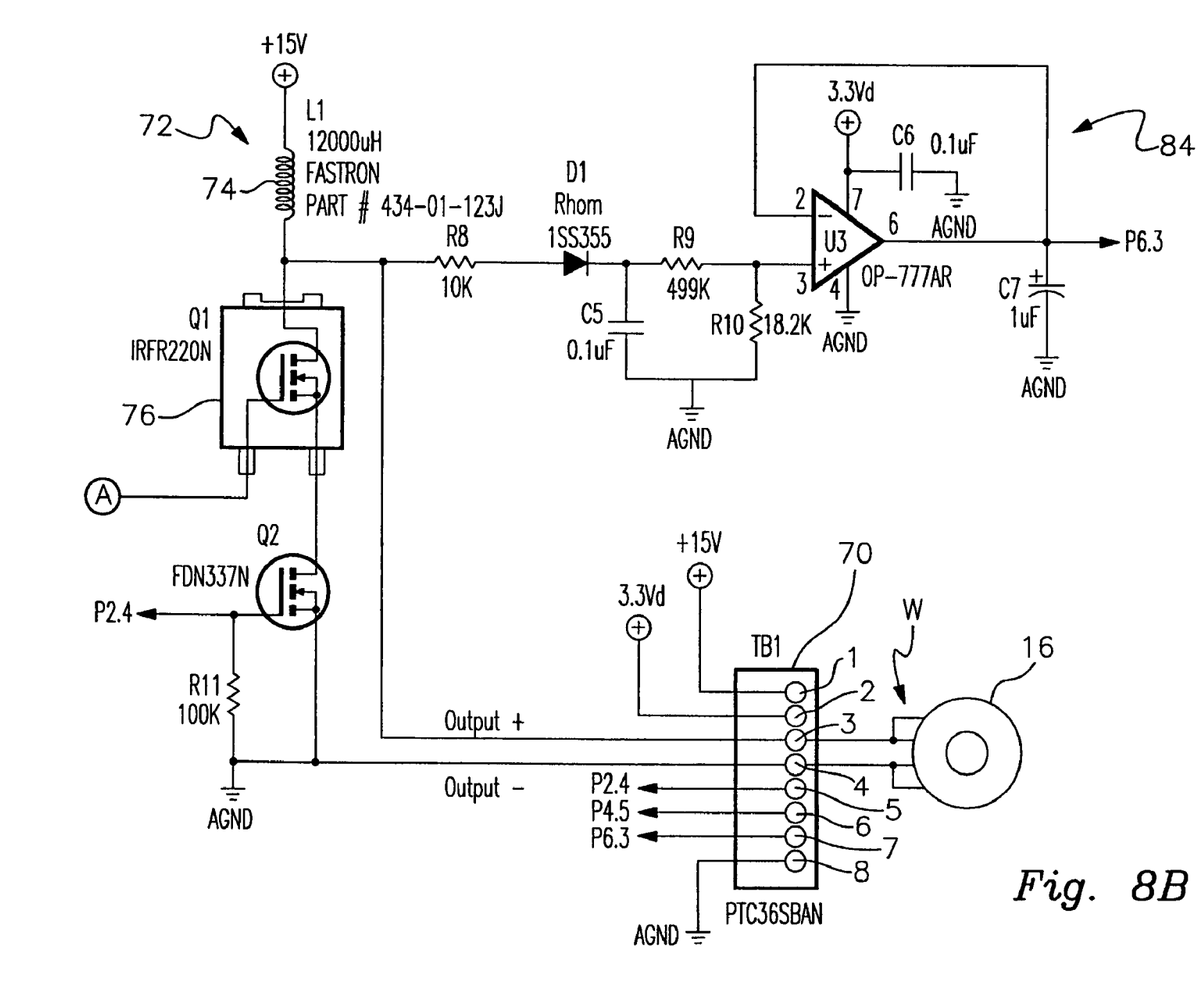

The transducer control circuit includes a contact strip 70, FIG. 8, which has eight contact pins 1-8. Pins 1 and 8 are connected to and provide power from the conventional principal power source (not explicitly labeled) of the turbidimeter or other instrument. In this version, 15 volts are delivered to a high voltage circuit 72. This circuit, which comprises a coil 74 and a MOSFET 76, increases the voltage to approximately 48 VAC peak-to-peak for use by the transducer in a manner described below. Pin 2 of contact strip 70 provides a lower voltage (e.g. 3.3 volts) to operate various components of control circuit 60 such as pulse width modulator 78, voltage controlled oscillator 80 and detection circuit 84.

Pin 6 of contact strip 70 provides a signal P4.5 from the CPU of the turbidimeter or other instrument to pulse width modulator 78, which converts the signal to DC voltage. This voltage is then delivered to oscillator 80, which functions as a voltage-to-frequency converter. A variable frequency output signal, which varies between approximately 30 and 55 KHz, is produced at output 5 of oscillator 80. This signal is transmitted to a buffer circuit 82, which controls the operation of gate G of transistor 76. As previously stated, circuit 72 increases the output voltage delivered from the main power source considerably. A high voltage alternating current signal is thereby provided to pins 3 and 4 of strip 70. The signal sweeps across the frequency range described above so that such a range of frequencies are delivered to the components of transducer 16 over wiring W. This sweep is performed over a span of approximately thirty seconds. During that time, the resonant frequency of the transducer-cuvette assembly is generated so that the transducer vibrates especially vigorously and particulate matter is dislodged from the glass surface of the cuvette or other glassware.

Detection circuit 84 monitors operation of the transducer and provides a signal P6.3 to pin 7, which indicates a problem with the cuvette or the cleaning system. In particular, a drastic change in the voltage produced by circuit 84 may reveal that a cuvette is missing, that one or more of the contact springs are broken or that no contact is being made between the springs and the transducer. Corrective action may then be taken.

It should be understood that in alternative embodiments, various other types of circuits and alternative electrical components known to persons skilled in the art may be employed to deliver an electrical signal to the transducer so that the transducer is vibrated to clean the glassware in the manner previously described. The particular components described in this circuit and the frequency and voltage levels described herein are intended to be illustrative only and do not constitute limitations of the invention.

In operation, circuit 60 remains continuously "on" during use of the turbidimeter or other water testing instrumentation with which system 10 is employed. As a result, a sweep of frequencies are delivered from control circuit 60 to transducer 16. As previously stated, this preferably includes the resonant frequencies of the transducer-cuvette assembly so that maximum vibration and optimum cleaning are achieved. More particularly, the transducer is supplied with a signal of approximately 50 volts (peak to peak) and the control circuit sweeps the frequency between 30 and 55 KHz to assure that the resonant frequency of each individual transducer-cuvette assembly is generated. This provides for maximal vibration and optimal cleaning of the glassware.

The use of the connector cap is particularly advantageous. The springs provide for flexible and yet positive interengagement and electrical contact between the control circuit and the transducer. As a result, the control circuit does not have to be "hard wired" to the transducer. The user is thereby able to freely rotate and/or remove the cuvette from the test instrument without having to remove or disengage wires or electrical connectors. In the context of the turbidimeter referenced above, it is also important for the user to periodically index the cuvette within the turbidimeter by axially turning the tubular glassware. Such indexing allows the turbidimeter to obtain the cleanest and most accurate readings through the glassware. The glassware also must be removed each time recalibration of the instrument is required. Because the cleaning system of the present invention is not hard wired, performing the necessary indexing (rotation) and glassware removal (for re-calibration) are facilitated considerably. When the glassware is indexed, the spring contacts simply slide across and remain in unbroken contact with the transducer. Removing the glassware disengages the contacts from the transducer and replacing the glassware after in the instrument is calibrated automatically re-engages the spring contacts with the transducer. No wiring or connectors must be manipulated for either procedure.

From the foregoing it may be seen that the apparatus of this invention provides for a system that automatically and continuously inhibits the buildup and growth of organic and inorganic particulates on optical test equipment glassware so that more reliable readings may be taken with reduced interruption of service. While this detailed description has set forth particularly preferred embodiments of the apparatus of this invention, numerous modifications and variations of the structure of this invention, all within the scope of the invention, will readily occur to those skilled in the art. Accordingly, it is understood that this description is illustrative only of the principles of the invention and is not limitative thereof.

Although specific features of the invention are shown in some of the drawings and not others, this is for convenience only, as each feature may be combined with any and all of the other features in accordance with this invention.

While the invention has been described with respect to preferred embodiments, those skilled in the art will readily appreciate that various changes and/or modifications can be made to the invention without departing from the spirit or scope of the invention as defined by the appended claims.

What is claimed is:

1. An optical measurement system with ultrasonically cleaned components, said system comprising:
    a cuvette defining an interior for holding a test sample, the cuvette having a first portion adapted and configured to engage a flow head and a second portion that is at least partially transparent;
    a flow head having a body defining a cap portion selectively engaged to the first portion for enclosing the interior of the cuvette, the flow head being adapted to direct the test sample into and out of the cuvette;
    an ultrasonic transducer permanently fastened to the cuvette, said transducer including material that vibrates when a selected voltage is applied to said transducer;
    a connector for establishing electrical contact with said transducer; and
    an ultrasonic control circuit for delivering an electrical signal with the selected voltage through said connector to said transducer such that said transducer vibrates to dislodge particulate matter from the at least partially transparent second portion of the cuvette and prevent particulate matter from collecting on the at least partially transparent second portion of the cuvette.

2. The system of claim 1 in which said connector includes a connector cap comprising a plurality of contacts for energizing said transducer.

3. The system of claim 2 in which said contacts are slidably engagable with said transducer to maintain electrical contact with said transducer when said transducer and the container are adjusted.

4. The system of claim 2 in which said contacts comprise spring contacts carried by an upper portion of said cap for electrically engaging said transducer, wherein the springs are longitudinally retractable within said cap.

5. The system of claim 1 wherein the transducer includes a piezoelectric disk and an aluminum disk juxtaposed against and secured to said piezoelectric disk and said connector includes an outer coil spring contact that is interengagable with said aluminum disk and a second inner coil spring contact that is interengagable with said piezoelectric disk.

6. The system of claim 2 in which said connector cap includes an annular wall surrounding said contacts for receiving said transducer and an attached lower end of the container, said wall for holding the container in place with said transducer engaging said contacts.

7. The system of claim 1 in which said control circuit includes an ultrasonic printed circuit board for operably mounting to a printed circuit board that controls operation of the testing equipment, said control circuit for being electrically powered by an operating circuit of the test equipment.

8. The system of claim 1 in which said control circuit generates signals having a series of frequencies, including the resonant frequency of said transducer and container to which said transducer is secured such that said transducer and container vibrate sufficiently to maintain the at least partially transparent portion of the container substantially free of particulate build-up.

9. The system of claim 8 in which said control circuit continuously and repeatedly sweeps through a predetermined series of frequencies.

10. The system of claim 1 in which said selected signal includes the resonant frequency of the transducer and cuvette to which said transducer is secured.

11. The system of claim 1 wherein the first portion is a threaded neck for engaging the flowhead.

12. The system of claim 1 further comprising: a measurement system having a light source for directing light through the second portion and test sample; and a sensor for measuring the light to determine turbidity of the test sample.

13. The system of claim 1 wherein the material includes: a vibration disk with a first diameter and secured to the container; a piezoceramic disk with a second diameter relatively smaller than the first diameter and secured to the vibration disk such that the ultrasonic control circuit is selectively connected thereto to provide the selected voltage and, in turn, create an ultrasonic vibration in the ultrasonic transducer.

14. An optical measurement system with ultrasonically cleaned components, said system comprising:
    a cuvette defining an interior for holding a test sample, the cuvette having a first portion adapted and configured to engage a flow head and a second portion that is at least partially transparent;
    a flow head selectively engaged to the first portion for enclosing the interior of the cuvette, the flow head being adapted to direct the test sample into and out of the cuvette;
    an ultrasonic transducer permanently fastened to the cuvette, said transducer including material that vibrates when a selected voltage is applied to said transducer;
    a connector for establishing electrical contact with said transducer;
    an ultrasonic control circuit for delivering an electrical signal with the selected voltage through said connector to said transducer such that said transducer vibrates to dislodge particulate matter from the at least partially transparent second portion of the cuvette and prevent particulate matter from collecting on the at least partially transparent second portion of the cuvette;
    wherein the connector includes:
    a base having a first surface and a second surface defining a recess;
    an annular lip upstanding from the first surface;
    an outer coil spring contact mounted on the first surface and having an end post passing through the base; and
    an inner coil spring contact mounted on the first surface within the outer coil spring contact and having an end post passing through the base, wherein each of the coil spring contacts is longitudinally retractable relative to the base and each of the end posts is in electrical communication with the ultrasonic control circuit.

15. The system of claim 14, further comprising means for coupling the glassware to the annular lip, wherein the means for coupling the glassware to the connector cap assembly is selected from the group consisting of an interference fit between the annular lip and glassware, threads and combinations thereof,
    wherein each of the coil spring contacts is ground flat on a second end, and
    wherein the base defines at least one drainage hole extending from the first surface to the second surface.

16. A turbidimeter comprising:
a) a measurement system including:
- i) a container defining an interior for holding a test sample, the container having a portion that is at least partially transparent;
- ii) a flow head having a body defining a cap portion selectively engaged to the container for enclosing the interior, the flow head being adapted to direct the test sample into the interior of the container;
- iii) a light source for directing light through the at least partially transparent portion and, thereby, the test sample in the interior of the container; and
- iv) a sensor for measuring the light passing through the test sample to determine a turbidity of the test sample; and b) an optical cleaning system including:
- i) an ultrasonic transducer permanently fastened to the container including material that vibrates when a selected voltage is applied thereto;
- ii) a connector for establishing electrical contact with said transducer; and
- iii) an ultrasonic control circuit for delivering an electrical signal with the selected voltage through said connector to said transducer such that said transducer vibrates to dislodge particulate matter from the at least partially transparent portion of the container and prevent particulate matter from collecting thereon.

17. A turbidimeter as recited in claim 16, wherein the container is a glass cuvette.

18. A turbidimeter as recited in claim 17, wherein the material is bonded to a bottom of the glass cuvette.

19. A system for ultrasonically cleaning glassware in optical testing equipment and measuring turbidity of a test sample, said system comprising:

a cuvette defining an interior for receiving a test sample;

a flow head having a body defining a cap portion selectively engaged to the cuvette for enclosing the interior, the flow head being adapted to direct a test sample into the cuvette;

a measurement system for directing light through the cuvette and measuring the light to determine turbidity the test sample;

an ultrasonic transducer permanently fastened to the cuvette, said transducer including material that vibrates when a selected voltage is applied to said transducer;

a connector for establishing electrical contact with said transducer; and an ultrasonic control circuit for delivering an electrical signal through the connector with the selected voltage through said connector to said transducer such that said transducer vibrates to dislodge particulate matter from the cuvette and prevent particulate matter from collecting therein.

20. The system of claim 1 further comprising a test sample in the interior of the cuvette.

* * * * *